United States Patent [19]
White

[11] 4,437,475
[45] Mar. 20, 1984

[54] TRANSVENOUS CARDIOVASCULAR INTEGRATED LEAD ANCHORING SLEEVE, PROTECTOR, AND PERMANENT LEAD INTRODUCER STOP GAP

[75] Inventor: David L. White, Wyoming, Minn.

[73] Assignee: Medtronic, Inc., Minneapolis, Minn.

[21] Appl. No.: 297,469

[22] Filed: Aug. 28, 1981

[51] Int. Cl.³ .............................................. A61N 1/04
[52] U.S. Cl. ................................... 128/785; 128/786; 128/419 P
[58] Field of Search .............................. 128/784–786, 128/419 P, 214.4; 604/178

[56] References Cited

U.S. PATENT DOCUMENTS

| 3,788,328 | 1/1974 | Alley et al. | 604/178 |
| 3,880,169 | 4/1975 | Starr et al. | 128/418 |
| 4,230,110 | 10/1980 | Beroff | 128/214.4 |
| 4,266,552 | 5/1981 | Dutcher et al. | 128/419 |
| 4,276,882 | 7/1981 | Dickhudt | 128/784 X |

OTHER PUBLICATIONS

Parsonnet et al., "The Natural History of Pacemaker Wires", J. Card. Surg., vol. 65, #2, Feb. 1973, pp. 315-322.
Lui, "Anchoring of Pacemaker Electrodes . . . ", Surgery, Mar. 1967, vol. 16, No. 3, pp. 380-381.
Exerpt from the Dec. 1978, Siemens-Elema Catalog entitled "The 'S' Generation Pacing Leads, Adapters and Accessories".

Primary Examiner—Lee S. Cohen
Attorney, Agent, or Firm—Reed A. Duthler; John L. Rooney; Joseph F. Breimayer

[57] ABSTRACT

A body implantable lead having an anchoring sleeve slideably affixed thereto. The anchoring sleeve is generally cylindrical in shape, having a cylindrical lumen through which the main body of the body implantable lead passes. Since the lumen within the anchoring sleeve is smaller than the diameter of the electrode fixation device at the distal end and the electrical connector at the proximal end of the body implantable lead, the anchoring sleeve is fixedly, though slideably attached to the body implantable lead. The anchoring sleeve is molded of a body compatible material such as silicone or polyurethane. Small serrations of body compatible material within the lumen of the anchoring sleeve generate sufficient friction such that the anchoring sleeve does not slide along the body implantable lead from the sheer force of gravity. The distal end of the anchoring sleeve is tapered or otherwise suitably shaped to permit it to occlude a permanent lead introducer and/or blood vessel during implantation. A groove about the body of the anchoring sleeve permits ready attachment through suturing.

4 Claims, 5 Drawing Figures

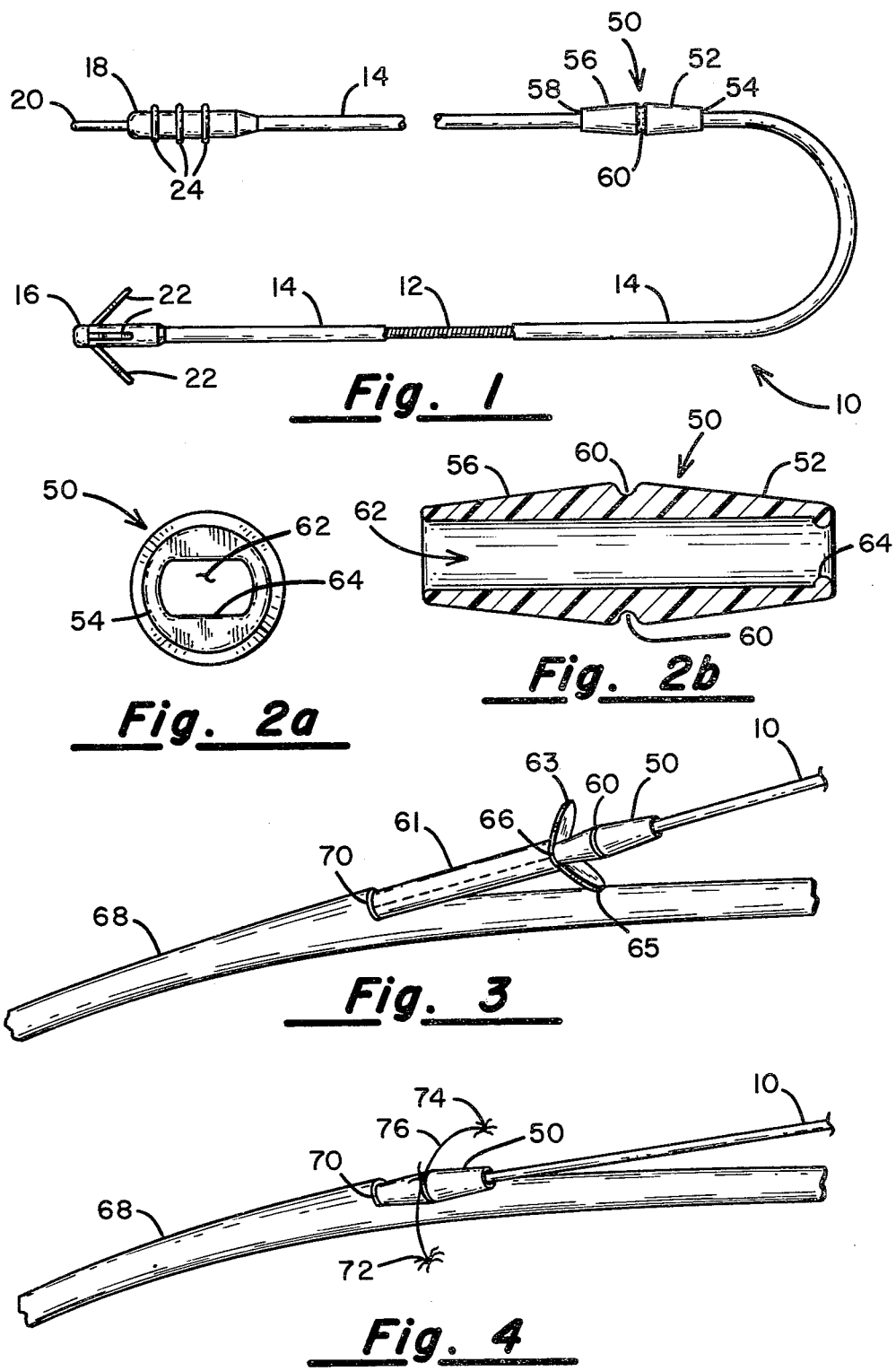

TRANSVENOUS CARDIOVASCULAR INTEGRATED LEAD ANCHORING SLEEVE, PROTECTOR, AND PERMANENT LEAD INTRODUCER STOP GAP

BACKGROUND OF THE INVENTION

1. Field of the Invention

The present invention relates generally to implantable medical devices, and more specifically relates to fixation apparatus and techniques for body implantable leads.

2. Description of the Prior Art

The earliest body implantable leads used for cardiac pacing were implanted on the outside surface of the heart. The first fixation means used were sutures wherein the electrode was sutured onto the epicardium. Subsequently, leads were made for epicardial use which had suturing pads which were permanently bonded to the body of the lead. U.S. Pat. No. 3,880,169 issued to Starr et al shows a myocardial electrode having a permanently bonded suturing pad. Characteristic of the suturing pad taught by Starr et al is that it is permanently affixed at a single position on the lead body. This is sufficient and even desirable for myocardial applications since the suturing pad is located in close proximity to the electrode. It is used to hold the electrode at the distal tip of the lead body in place against the myocardial tissue.

The substantial popularity of the transvenous type lead has led to a different type of problem. Since the lead is inserted into a vein at a position quite distant from the heart, the lead body must be secured in place at this remote location. The result is that the suturing sleeve to be used in transvenous applications cannot be located at a fixed distance from the distal end of the lead since the distance from the insertion point in the vein to the final implant position of the distal tip varies substantially from patient to patient and will even vary for a given patient depending upon the exact implant procedure used.

The earliest technique used in suturing transvenous leads was to suture directly across the lead body itself and to the vein or surrounding tissue in the vicinity of the veinectomy. This procedure proved satisfactory for silicone rubber type leads. However, with the advent of urethane leads, it has been found that the lead body may be substantially damaged by sutures applied in direct contact with the insulating sheath. This problem is further compounded by the use of relatively softer conductor coils such as drawn brazed strand.

An attempt to overcome this problem is discussed by Dutcher et al in U.S. Pat. No. 4,266,552. This reference teaches a lead anchoring bobbin which accepts a transvenous pacing lead that is frictionally engaged about two opposed disc-shaped elements. The lead anchoring bobbin is then sutured in place. The normal manner of using this invention is to frictionally engage the body of the transvenous pacing lead in the vicinity of the veinectomy and suture it directly in place to adjacent muscle tissue.

The major problem that has developed with the use of the lead anchoring bobbin is that the device must be secured in place using two hands of the attending physician. Two hands are required because the lead body must actually be wrapped around the lead anchoring bobin. This problem is further complicated when, with the use of a permanent lead introducer, the proximal end of the introducer must normally be occluded with the thumb to prevent air embolisms and to curtail the bleeding that is present. After the permanent lead introducer is removed, the vein itself must be occluded acutely to contain the bleeding.

SUMMARY OF THE INVENTION

The present invention overcomes the problems inherent in the prior art apparatus and techniques by employing a suturing sleeve which is permanently attached about the lead body. This is accomplished by using a generally cylindrical member having a central lumen through which the main lead body passes. Unlike the earlier suturing pads which were permanently affixed at a given position, the present invention teaches an anchoring sleeve which is slideably mounted on the main lead body. Because the central lumen of the anchoring sleeve is smaller than the electrical connector at the proximal end of the lead body and the electrode fixation means assembly at the distal end, the anchoring sleeve is permanently attached to the lead body even though it is slideable thereon.

Small serrations within the central lumen of the anchoring sleeve increase the friction between the anchoring sleeve and the main lead body to the extent that the anchoring sleeve does not slide by mere force of gravity alone. It must be physically moved by direct manual intervention. The distal end of the anchoring sleeve is shaped in such a fashion that it is easily used to occlude the proximal end of a permanent lead introducer should this implant procedure be used. After the permanent lead introducer has been removed, the anchoring sleeve is placed in its permanent position. The distal end of the anchoring sleeve may then be used to occlude the vein at the point of the veinectomy to cause acute and chronic sealing of the entry point. A central groove is used to assist in holding the suture material in the proper position.

BRIEF DESCRIPTION OF THE DRAWINGS

FIG. 1 is a plan view of a transvenous pacing lead containing an anchoring sleeve according to the teaching herein.

FIG. 2a is an end view of the anchoring sleeve as viewed from the distal end.

FIG. 2b is a side sectional view of the anchoring sleeve.

FIG. 3 shows the anchoring sleeve occluding the proximal end of the permanent lead introducer.

FIG. 4 shows the chronic implantation of the anchoring sleeve with sutures in place.

DETAILED DESCRIPTION OF THE PREFERRED EMBODIMENT

The present invention is described in terms of an anchoring sleeve currently being employed on the urethane transvenous pacing leads of the assignee of this invention. Those of ordinary skill in the art will be readily able to apply this invention to other requirements using the teachings contained herein and within the scope of the claims hereto appended.

FIG. 1 is a plan view of a transvenous pacing lead having an anchoring sleeve according to the present invention slideably attached thereto. The transvenous pacing lead generally designated 10 contains a main lead body having polyurethane insulation 14 insulating an inner conductor coil 12 shown in the cutaway portion. Inner conductor 12 is preferably a quadrafilar coil of drawn brazed strand wire having six outer strands of MP35N and an inner matrix of silver. The distal end of transvenous pacing lead 10 contains tines 22 which are discussed in commonly assigned U.S. Pat. No. 3,902,501 issued to Citron et al. An electrode 16 of platinum iridium alloy having an effective surface area of approximately 8 mm square is positioned at the very distal tip and is electrically coupled to inner conductor coil 12.

The proximal end of transvenous pacing lead 10 contains an electrical connector assembly comprised of an insulating conductor body 18 having multiple sealing rings 24. Terminal pin 20 is an electrically conducting metallic conductive surface electrically coupled to inner conducting coil 12.

Anchoring sleeve 50 is made of a body compatible material such as urethane or silicone rubber. The preferred embodiment anchoring sleeve 50 is made from silicone rubber because of the added strength supplied. A centrally located groove 60 is adapted to receive the suture thread. The distal end of anchoring sleeve 50 contains taper 52 which ends at surface 54. The maximum diameter of anchoring sleeve 50 is greater than the diameter of the current lead introducer normally used with this type of lead and is likewise greater than the vein to be sacrificed in the implant procedure. Similarly, distal surface 54 has a diameter substantially less than the permanent lead introducer and the vein to be sacrificed. The preferred maximum diameter for anchoring sleeve 50 is approximately 4.0 mm. The preferred diameter of distal surface 54 is 3.2 mm. This difference in diameter is very important since it permits taper 52 to readily occlude the 10½ french permanent lead introducer and also the vein to be sacrificed in the implant procedure.

The proximal end contains taper 56 which reduces to proximal surface 58. In the preferred embodiment the proximal and distal portions of anchoring sleeve 50 are symmetrical. This provides a compliant strain relief for the lead. As explained above, anchoring sleeve 50 contains a central lumen between distal surface 54 and proximal surface 58 which is slightly larger than insulating sheath 14. However, this central lumen is smaller than connector body 18 and also smaller than tines 22 or electrode 16. Therefore, anchoring sleeve 50 must be positioned over insulating sheath 14 before both proximal and distal tips of transvenous pacing lead 10 are permanently in place.

FIG. 2a is a view from the distal end of anchoring sleeve 50. Central lumen 62 is of sufficient size to permit anchoring sleeve 50 to readily slide about insulating sheath 14 as explained above. To prevent the repositioning of anchoring sleeve 50 from the force of gravity, lip 64 is located within lumen 62 to provide additional frictional engagement with insulating sheath 14. Lip 64 is dimensionally controlled such that anchoring sleeve 50 may be readily slideable over insulating sheath 14 using slight manual force.

FIG. 2b is a side sectional view of anchoring sleeve 50. Shown are taper 52, groove 60, and lip 64.

FIG. 3 is a view in the vicinity of the veinectomy. Vein 68 has been entered through an incision at point 70. Permanent lead introducer 61, containing proximal manual attachment members 63 and 65 has been inserted into vein 68. Transvenous pacing lead 10 has been inserted into lumen 66 of permanent lead introducer 61 and into vein 68. Of course, the distal end of transvenous pacing lead 10 containing electrode 16 and tines 22 is inserted into lumen 66 of permanent lead introducer 61 and from there into vein 68. While transvenous pacing lead 10 is being properly positioned within the heart, the distal end of anchoring sleeve is securely inserted into lumen 66 of permanent lead introducer 61. The taper 52 will thus occlude the proximal end of lumen 66 thereby preventing excessive bleeding and possible air emboli.

FIG. 4 is a view after the permanent lead introducer has been removed and transvenous pacing lead 10 permanently positioned. Taper 52 of anchoring sleeve 50 is now used to occlude incision 70 of vein 68. Again, this prevents excessive bleeding and possible air emboli. Anchoring sleeve 50 is then sutured into place, using the suture 76 which goes about groove 60 and is sutured directly into muscle tissue at points 72 and 74.

Having thus described the preferred mode of practicing the present invention as employed within the product line of the assignee of the present invention, those of skill in the art will be readily able to use the present invention within other configurations within the scope of the claims hereinafter appended.

What is claimed is:

1. A body implantable lead comprising:
   a conductor having a proximal end and a distal end;
   an insulating sheath of body compatible material having an outside diameter, covering said conductor;
   an electrode having an outside diameter greater than the outside diameter of said insulating sheath, coupled to said distal end of said conductor;
   an electrical connector having an outside diameter greater than the outside diameter of said insulating sheath, coupled to said proximal end of said conductor; and
   an anchoring sleeve fabricated of a pliant, compressible material, having a proximal end, a distal end, a circumferential suture groove completely encircling said anchoring sleeve and a lumen with an inside diameter greater than the outside diameter of said insulating sheath, through which said insulating sheath passes, said electrode and said electrical connector each having an outside diameter greater than the inside diameter of the lumen of said anchoring sleeve whereby said anchoring sleeve is permanently attached and slideably mounted about said insulating sheath.

2. A body implantable lead according to claim 1 wherein the circumferential groove of said anchoring sleeve is located intermediate the proximal and distal ends of said anchoring sleeve, and wherein said anchoring sleeve has a first outside diameter, at the circumferential groove of said anchoring sleeve, said anchoring sleeve having a second outside diameter, less than said first outside diameter, at the distal end of said anchoring sleeve and a third outside diameter, less than said first outside diameter at the proximal end of said anchoring sleeve, said anchoring sleeve tapering smoothly from said first outside diameter to said third outside diameter and from said first outside diameter to said second outside diameter.

3. A body implantable lead comprising:
   a conductor having a proximal end and a distal end;
   an insulating sheath of body compatible material, having an outside diameter, covering said conductor;
   an electrode coupled to said distal end of said conductor;

an electrical connector coupled to said proximal end of said conductor; and an anchoring sleeve having a proximal end, a distal end, and a lumen with an inside diameter which is at least as large as said outside diameter, through which said insulating sheath passes, said anchoring sleeve having a first outside diameter located intermediate the proximal and distal ends of said anchoring sleeve, having a second outside diameter less than said first outside diameter at the distal end of said anchoring sleeve and having a third outside diameter less than said first outside diameter at the proximal end of said anchoring sleeve, said anchoring sleeve tapering smoothly from said first outside diameter to said second and third outside diameters, said anchoring sleeve further having a circumferential suture groove completely encircling said anchoring sleeve at the location of said first outer diameter.

4. A body implantable lead according to claim 3 wherein said inside diameter of said lumen of said anchoring sleeve is greater than said outside diameter of said insulating sheath.

* * * * *